US008529632B2

(12) United States Patent
Klawitter et al.

(10) Patent No.: US 8,529,632 B2
(45) Date of Patent: Sep. 10, 2013

(54) THUMB METACARPAL IMPLANT

(75) Inventors: Jerome J. Klawitter, Austin, TX (US); Joseph P. Ritz, Austin, TX (US); Monti R. Gourley, Austin, TX (US); Ashley Degrood, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 123 days.

(21) Appl. No.: 13/063,590

(22) PCT Filed: Sep. 17, 2009

(86) PCT No.: PCT/US2009/057301
§ 371 (c)(1), (2), (4) Date: Mar. 11, 2011

(87) PCT Pub. No.: WO2010/033691
PCT Pub. Date: Mar. 25, 2010

(65) Prior Publication Data

US 2011/0172782 A1 Jul. 14, 2011

Related U.S. Application Data

(60) Provisional application No. 61/097,597, filed on Sep. 17, 2008.

(51) Int. Cl.
*A61F 2/42* (2006.01)

(52) U.S. Cl.
USPC .......... 623/21.15

(58) Field of Classification Search
CPC . A61F 2/42; A61F 2/4241; A61F 2002/4241; A61F 2002/4256; A61F 2002/4258
USPC .......... 623/21.11–21.17
See application file for complete search history.

(56) References Cited

U.S. PATENT DOCUMENTS

| | | | | |
|---|---|---|---|---|
| 4,276,660 | A | 7/1981 | Laure | |
| 4,944,758 | A * | 7/1990 | Bekki et al. | 623/21.15 |
| 4,955,916 | A | 9/1990 | Carignan et al. | |
| 5,507,822 | A * | 4/1996 | Bouchon et al. | 623/21.16 |
| 5,702,469 | A | 12/1997 | Whipple et al. | |
| 7,182,787 | B2 | 2/2007 | Hassler et al. | |
| 2005/0033426 | A1 | 2/2005 | Ogilvie et al. | |
| 2005/0251265 | A1 | 11/2005 | Calandruccio et al. | |

OTHER PUBLICATIONS

Written Opinion of the International Searching Authority.

* cited by examiner

*Primary Examiner* — Thomas J Sweet
*Assistant Examiner* — Megan Wolf
(74) *Attorney, Agent, or Firm* — Fitch, Even, Tabin & Flannery LLP

(57) ABSTRACT

A hemi-arthroplasty implant (11) joint replacement for the base of the first metacarpal of the CMC joint is created which can effectively restore and reestablish functional joint mechanics. The implant (11) has a unique head section (13) creating a particular interrelation between a spherical head articular surface (19), that is received in a surgically prepared cavity in the trapezium, wherein a supporting neck (21) in a re-entrant region joins the head to a flat, generally oblong collar (15).

14 Claims, 3 Drawing Sheets

FIG. 8C
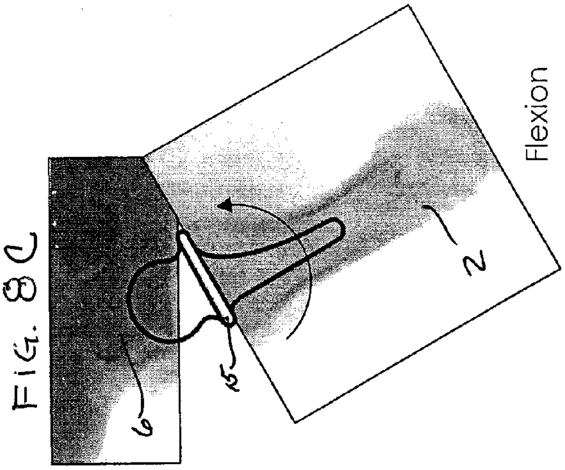
FIG. 8B
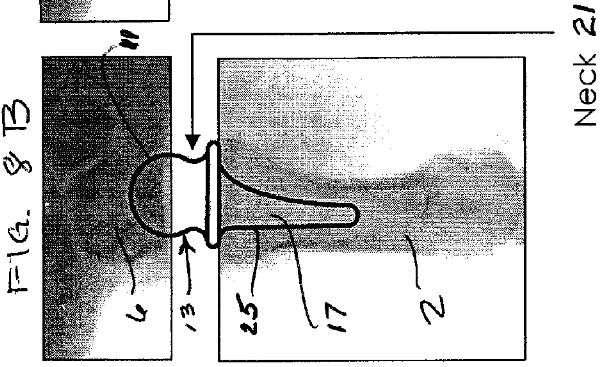
FIG. 8A
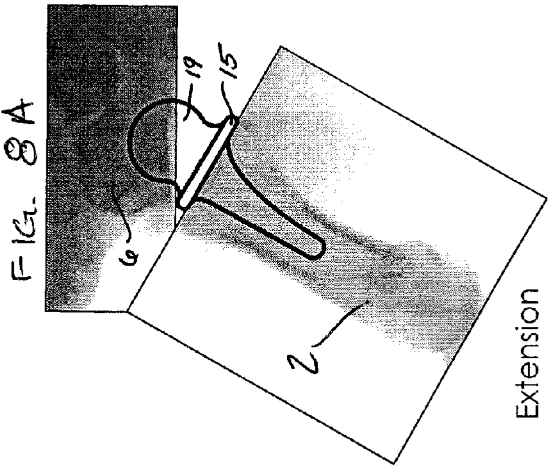
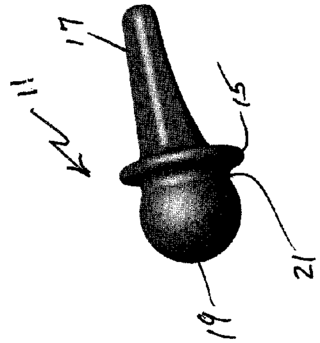
FIG. 7

THUMB METACARPAL IMPLANT

This application claims priority from U.S. Provisional Patent Application Ser. No. 61/097,597, filed Sep. 17, 2008.

This invention relates to implants designed for the proximal end of the thumb metacarpus and, more particularly, to an implant for insertion into the resected proximal end of the thumb metacarpus, having a head that will articulate with a surgically prepared cavity in the trapezium to effect a hemi-arthroplasty of the thumb carpometacarpal (CMC) joint.

BACKGROUND OF THE INVENTION

Overall, the design and manufacture of a functional, robust, and durable joint prosthesis is a complex and multi-faceted problem involving anatomical, biocompatibility, biomechanical, and surgical considerations. From a functional perspective, mechanical design considerations should address the joint range of motion, center of rotation, force-transmission-capabilities, and wear resistance of the component. Anatomical issues for consideration involve the shape of the intramedullary stem and of the articulating surface, and the need for a range of sizes to accommodate anthropomorphic variations. Surgical concerns should take into account the need for appropriate instrumentation utilized during the implantation procedure to facilitate an accurate osteotomy, effect minimal bone removal, and preserve surrounding soft tissues. The design objective for such an implant to replace the distal articular surface of a diseased and/or damaged CMC joint should be to relieve pain, allow maximum range of motion, and restore to the patient a high degree of hand functionality. Size and geometric features of the component are in a large way dictated by morphometric measurements of the natural CMC joint; however, the ultimate component should be such that it will exhibit longevity when subjected to rigorous and demanding anatomically relevant constraint and loading situations.

There have been a number of complete CMC joint implants wherein implants described and marketed having articulating surfaces have been surgically inserted into both the base of the first metacarpal and the trapezium. Examples of these are found in U.S. Pat. Nos. 4,276,660; 4,955,916; 5,645,605; and 5,702,469. Other alternatives include replacing the entire trapezium, either along with the base of the metacarpus (see U.S. Patent Publication No. 2005/0251625) or by itself (see U.S. Patent Publication 2007/0021839). Still other alternatives which constitute hemi joint replacements include the various prior art implants described in U.S. Pat. No. 7,182,787 and the implant described in U.S. Patent Publication 2005/0033426.

Despite the wide variety of prospective solutions to the all too frequently occurring problem of a deteriorated joint at the base of the thumb metacarpus, the search has continued for still further, even more improved solutions for hemi joint replacement.

BRIEF SUMMARY OF THE INVENTION

It has been found that a particularly stable joint, which will exhibit resistance to joint subluxion and dislocation, can be achieved through the combined effect of three design features of an implant to be employed in a procedure wherein an articulating surface is provided in the form of a spherical cavity by surgically adapting the trapezium to serve as a socket which receives the head of an implant that is seated in the resected end of the base of the thumb metacarpus. Although this basic concept has previously been employed, it has now been found to be truly effective in providing the full range of motion and stability as a result of the careful design of the head region of the implant that is seated in the base of the resected metacarpus. It has been found that, by capture of about one-third to one-half of the spherical region of a spherical head of an implant having a head region incorporating these three design features in combination, a significantly improved hemi-arthroplasty is facilitated. These features interrelate a head section that includes a head and a neck, together with a base collar, which interface with the trapezium during flexion and extension while allowing circumduction and axial rotation at the joint, and a medullary stem which is offset from the head section and collar which provides fixation of the implant to the metacarpus.

In one particular aspect, the invention provides a hemi-arthroplasty implant for the base of the first metacarpal of the thumb CMC joint, said implant including a head section, a flat collar and a stem section, which head section comprises a spherical head and a neck section which connects said head to said flat collar, said neck section comprising an arcuate surface of circular cross section which extends between said spherical head and said flat collar, said neck section having a diameter N at its narrowest point of at least about 5% less than the head spherical diameter, and said flat collar being of noncircular, generally oblong shape having a dorsal edge, a volar edge and two lateral edges, with its dorsal width (DW) being equal to between 95% and 130% of lateral width (LW).

In another particular aspect, the invention provides a hemi-arthroplasty implant for the base of the first metacarpal of the thumb CMC joint, said implant including a head section, a flat collar and a stem section, which head section comprises a spherical head and a neck section of re-entrant curvature that connects said head to said flat collar, said neck section comprising an arcuate double-curved surface of circular cross section with its narrowest diameter N being at least about 10% less than the head spherical diameter H, said flat collar being of oblong shape having a dorsal edge, a volar edge and two lateral edges, with its dorsal width (DW) being greater than its lateral width (LW), and the axial length (Y) of said head section from the proximal surface of said flat collar to the tip of said spherical head is equal to between about 60% and 100% of the spherical diameter H and wherein the diameter N is equal to about 0.95 Y.

In a further particular aspect, the invention provides a hemi-arthroplasty prosthesis for the base of the first metacarpal of the thumb CMC joint, said implant including a head section, a flat collar and a stem section, which head section comprises a spherical head and a neck section which connects said head to said flat collar, said spherical head being centered on said collar in both the dorsal/volar and lateral directions, said neck section having an arcuate surface of circular cross section the narrowest diameter N of which is at least about 5% less than the head spherical diameter H, and said flat collar being of oblong shape having a dorsal edge, a volar edge and two lateral edges, with its dorsal width (DW) being equal to between 95% and 130% of its lateral width (LW), and said stem having a rectilinear dorsal surface which is essentially planar and which is spaced apart from a parallel plane that is tangent to said spherical head a distance equal to between 9% and 20% of said head diameter H.

In yet another particular aspect, the invention provides a method of repairing a CMC joint, which method comprises the steps of:

(a) resecting the base of the metacarpal bone, (b) surgically cutting a socket of spherical curvature in the trapezium to leave a rim of at least 2 mm about said socket, (c) implanting the stem section of a prosthesis as described above in one of such particular aspects in the medullary canal of said resected metacarpal bone, and (d) placing the spherical head of said prosthesis in said trapezium socket.

BRIEF DESCRIPTION OF THE DRAWINGS

FIG. 7 is a perspective view of the implant of FIGS. 3-6 reduced in size.

FIGS. 8A-8C are three schematic views showing the implant of FIGS. 3-7 and illustrating flexion/extension range of motion.

DETAILED DESCRIPTION OF THE PREFERRED EMBODIMENTS

Figure 2:
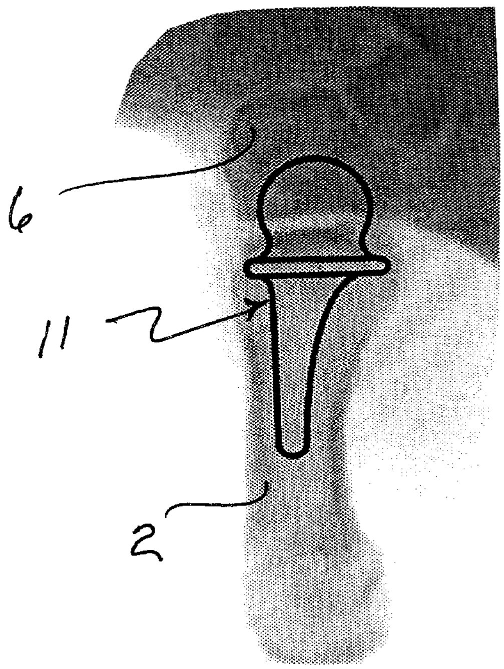
FIG. 2 is a lateral radiograph view of a hemi-arthroplasty implant embodying various features of the present invention.
Figure 1:
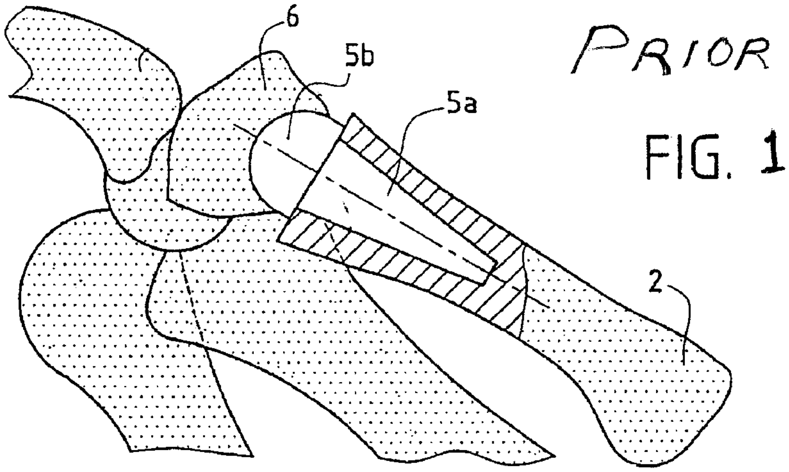
FIG. 1 is a schematic view of a hemi-arthroplasty implant for the base of the first metacarpal of the thumb CMC joint in accordance with the prior art.

FIG. 1 illustrates a prosthesis made in accordance with the prior art having a stem 5*a* which is implanted in the resected proximal end of the metacarpus 2 and having a head 5*b* that is received in a surgically prepared cavity in the trapezium 6. FIG. 2 illustrates a prosthesis or implant 11 embodying features of the present invention shown similarly implanted for purpose of comparison.

Figure 3:
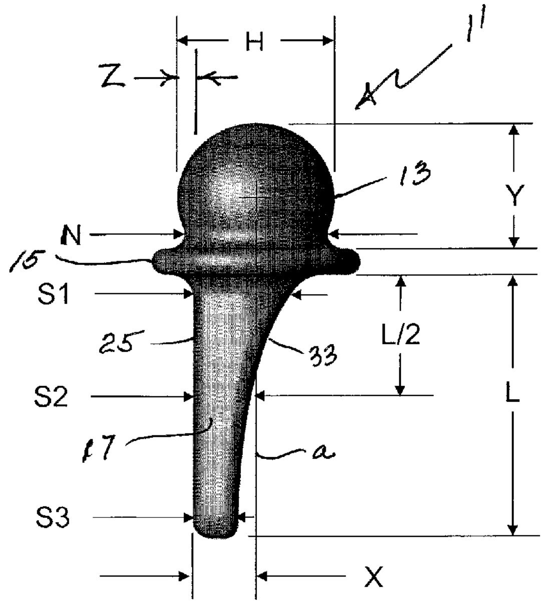
FIG. 3 is a lateral view of the implant of FIG. 2 enlarged in size.

As best seen in FIG. 3, one embodiment of the prosthesis 11 has a head section 13, a flat collar 15 which provides a base for the head section and a stem 17. The head section 13 includes a spherical articular head 19 which is connected by a neck 21 to the proximal surface of the flat collar 15; the intramedullary stem 17 extends from the rear or distal surface of the flat collar. The prosthesis 11 is designed to be implanted in the medullary canal of the first metacarpus 2 after removing the base of that bone. By providing the prosthesis 11 in four different sizes of heads and stems, it is expected that the full range of the human anatomy will be covered.

The prosthesis 11 should be made of a material that is biocompatible as to not result in adverse tissue reactions. Materials such as cobalt-chromium alloys, titanium alloys, polyethylene, silicone rubber and pyrolytic carbon have heretofore been successfully used to produce biocompatible finger joint implants. Finger joint implants produced using various of these materials have been shown to be particularly strong and durable; however, either (a) metal alloys or (b) pyrolytic carbon-coated ceramics or metal alloys are preferred.

For constructing one embodiment of the prosthesis 11, a machined graphite substrate is presently particularly preferred which is coated overall with a completely encasing pyrocarbon layer. The pyrocarbon layer encases the graphite substrate and thus provides the external surface of the implant which interfaces with bone and soft tissues in the reconstructed joint. Pyrocarbon exhibits a number of attributes deemed very desirable for an orthopedic prosthesis. These characteristics include: (1) high strength, (2) high wear resistance, (3) resistance to cyclic fatigue, (4) biocompatibility (with both blood and bone), (5) a modulus of elasticity similar to cortical bone, (6) an ability to support direct bone apposition, and (7) low friction on polished surfaces. Although various medically approved, dense pyrocarbons may be used, such as that sold under the trademark Pyrolite, pyrocarbon that is made in accordance with the teachings of U.S. Pat. No. 5,677,061 is particularly preferred; such is commercially available as On-X pyrocarbon.

The pyrocarbon layer, which preferably completely encapsulates such a graphite substrate formed from dense, isotropic, fine grain graphite, differs from it in mechanical properties; dense pyrocarbon is both stiffer and more fracture-resistant than a substrate machined, e.g. from POCO AXF-5F Biomedical Grade Graphite having a density greater than 1.75 g/cc. As a result, the exterior pyrocarbon layer dominates the mechanical and biocompatibility characteristics of the implant and provides the desired strength, durability, extreme resistance to wear, and both biological and biomechanical compatibility. Because pyrocarbon is not easily visible on radiographs, the graphite substrate may be machined from a material that is impregnated with a small amount of tungsten, e.g. 10 weight percent which is approximately 1 atomic percent, to render the graphite substrate radiopaque and thus clearly visible on radiographs.

More specifically, the articular head 19 is polished to a mirror finish so as to have an average surface roughness of about 8 microinches or less, e.g. an $R_A$=5.7±2.3 microinch (145±0.59 nm). In the presence of a lubricating medium, such as synovial fluid, such a mirror finish results in very low friction during articulation. Conversely, the stem 17 of the implant is not polished, and it may have a surface finish of essentially that produced during the pyrocarbon layer fabrication process, e.g. approximately 15 microinch (389 nm). The stem 17 preferably has a matte appearance and possesses a surface structure capable of achieving direct bone apposition.

Joint stability (resistance to joint subluxation and dislocation) for the implanted prosthesis is achieved by the combined effect of the design of the head section and the bone socket where the spherical head 19 is captured in a mating spherical cavity which is surgically created in the trapezium 6. The depth of the cavity should be equal to about one-third to one-half the spherical diameter of the head 19. Capture of one-third to one-half of the spherical head 19 provides a substantial mechanical capture of the head in the trapezium 6 and thus results in good resistance to subluxation and/or dislocation of the implant. The mating spherical cavity is created in the trapezium 6 using a spherical bone cutting burr; it should be centered in the articular surface of the trapezium. The spherical cavity is preferably made directly in the articular surface of the trapezium without resecting bone from the remainder of the trapezium. The diameter of the spherical cavity created in the trapezium 6 should be smaller than width of the trapezial bearing surface so that there will remain a rim of trapezial bone about 2-3 mm wide which surrounds the cavity in the trapezium. Such a 2-3 mm rim of bone surrounding the trapezial cavity provides buttressing strength to the cavity and allows it to support implant loading.

Excellent circumduction and axial rotation motions at the CMC joint following reconstruction with the prosthesis 11 are achieved as a result of the design of the head section 13, which is carefully designed to allow the implant spherical head to rotate in the mating spherical cavity created in the trapezium 6. The result is essentially a ball and socket articulation. However, it is the overall design including the re-entrant shape of the head section 13 at its neck 21 and the shape of the collar 15 which allow full range of motion of the CMC joint following arthroplasty.

The prosthesis 11 is implanted in the medullary canal of the metacarpus 2 after a portion of the base of the metacarpal bone has been surgically resected. The osteotomy creating the resection is made normal to the long axis of the metacarpus 2, and the removal results in a "gap" between the resected base of the metacarpal bone and the remaining articular surface of the trapezium 6. A spherical socket is surgically created in the trapezium 5 to receive the head 19 of the prosthesis. The re-entrant shape of the head section 13 and the size of the gap between the metacarpal bone and the trapezium 6 combine to allow for normal joint flexion/extension and abduction/adduction ranges of motion; such are illustrated in the three schematic views in FIGS. 8A, 8B and 8C. The re-entrant geometry of the spherical head section 13 at the location of the neck is important; its construction results in a precisely located neck 21 having an arcuate surface of circular cross section, which neck joins the spherical head 19 to the collar 15 of the prosthesis. The narrowest diameter N of the short neck 21 is at least 5% less, and preferably at least 10% less than the spherical diameter H of the head (FIG. 3). Preferably, the diameter N is not less than 75% H, and more preferably it is not less than 80% H. The cross section of the neck is that of a circle that lies in a plane perpendicular to the centerline of the implant; the centerline passes through the center of the sphere 19 and through the geometric center of the collar 15, i.e. the line "a" in FIG. 3. The diameter of the smallest circle cut by a plane perpendicular to the centerline "a" is the diameter N at the narrowest point of the neck 21. It has been found that the combination of this dimension, coupled with the total axial length of the head/neck (see dimension Y), the shape of the implant flat collar and the re-entrant shape at the neck, produce a particular amount of free space between the metacarpus 2 and the trapezium 6 that allows the desired substantial rotational motion without impingement, i.e. before the collar 15 impinges against a surface of the trapezium 6. The arcuate shape of the neck 21 is preferably that of a double-curved surface, i.e. one which is curved in two perpendicular planes; more preferably the neck surface is a section of a generally toroidal surface, i.e. a surface that closely approaches that of a torus so as to be within 10% of such a shape.

Fixation of the prosthesis in the metacarpus is achieved by means of the medullary stem 17 and the collar 15. The stem 17 of the prosthesis is shaped to fit into the medullary cavity of the proximal end of the thumb metacarpal bone. The stem 17 preferably has a shape that approximates the medullary cavity of the native metacarpus 6, and its length is approximately one-half the length of the metacarpus. The stem cross section is preferably asymmetrical about its long axis so that the prosthesis will resist axial rotation (rotation about its long axis).

The shape of the stem 17 and the location of the stem with respect to the flat collar 15 are design features that allow the stem (a) to properly fill the medullary cavity of the first metacarpal bone 2 so as to achieve stable fixation and (b) to precisely locate the spherical articular head 19 with respect to a socket surgically made centrally in the trapezium 6 and thus ensure proper alignment of the first metacarpal and trapezial bones. Moreover, the achievement of such location and the shape/proportioning of the implant 11 assures CMC joint movement such that the collar 15 avoids contact with any adjacent bone other than the trapezium. The shape and location of stem 17 with respect to the collar 15 is generally established to conform to the anatomy of the first metacarpal bone, which bone is essentially symmetric about its long axis when viewed dorsally but which is asymmetric about its long axis in the lateral view, as can be seen in FIG. 2. The dorsal cortex of the first metacarpal is essentially parallel to the long axis of the first metacarpal, and the osteotomy creating the resection of the base of the first metacarpal is carried out to be essentially perpendicular thereto. The volar cortex of the first metacarpal is asymmetric with respect to the long axis of the first metacarpal; it flares away from the first metacarpal long axis as the cortex approaches the base of the first metacarpal, as seen in FIG. 2. The desired alignment is obtained by forming the stem 17 with a rectilinear, essentially planar, dorsal surface 25 and by spacing this surface a specific distance from a plane parallel thereto which plane is tangent to the spherical head 19. This dimension is labeled Z in FIG. 3; it should be between 0.09 H and 0.20 H, with H being the spherical diameter of the head 19 to locate the spherical head in optimal position and assure desired ranges of motion.

Figure 6:
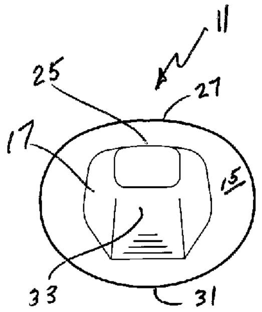
FIG. 6 is a view of the implant of FIG. 3 when seen from the distal end thereof which will be seated in the resected metacarpus.
Figure 5:
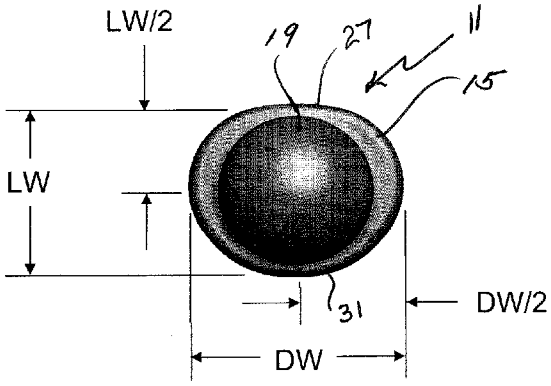
FIG. 5 is a front end view of the implant of FIG. 3 when seen from the proximal end thereof which will be received in a cavity surgically created in the trapezium.

The flat collar 15 resists any further axial movement of the prosthesis into the metacarpal bone following its implantation; such axial movement is often referred to as "subsidence". The collar 15 which is located between the head section 13 and the stem 17 has a dorsal edge, a volar edge and two lateral edges. The flat collar 15 is preferably noncircular, generally oblong in shape, when viewed looking along the long axis of the stem 17 as seen in FIGS. 5 and 6. The collar has an overall dorsal width DW, i.e. viewed from a dorsal perspective and a lateral width LW, i.e. when viewed laterally; the DW may be equal to between 95% and 130% of the LW. Preferably, the DW of the collar is about 10% to 30% greater than its LW. More preferably, it is at least 15% greater, and most preferably it is equal to 1.2 LW or more. Such a generally oblong shaped collar 15 may be particularly advantageous in matching the shape of the metacarpal bone so that the collar 15 will rest on the dense cortical bone, in order that it will best resist potential subsidence of the prosthesis into the metacarpal bone; it is also advantageous so that it will appropriately interengage with the trapezium 6 during articulation as seen in FIGS. 8A and 8C. The collar 15 is shaped to have a shallower curvature along its dorsal edge 27 and a more arcuate curvature along its volar edge 31 as best seen in FIG. 6. The dorsal edge curvature is at least 20% shallower than that of the volar edge, i.e. the dorsal edge radius of curvature is at least 20% longer. Overall, the shaping and proportioning of the collar 15 are selected that it engages the trapezium 6 as desired at the end of joint motion in either direction but carefully avoids contact with adjacent bones.

Figure 4:
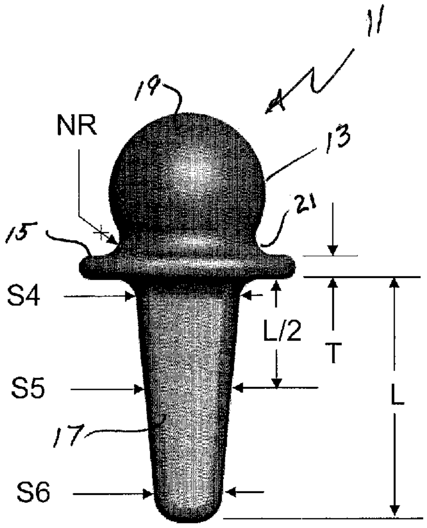
FIG. 4 is a dorsal view of the implant shown in FIG. 3.

As shown in FIG. 5, the spherical articular head 19 is essentially centered on collar 15. The dorsal surface 25 of stem 17 is essentially rectilinear and oriented perpendicular to the collar 15; it is essentially planar, having no more than some very shallow curvature. The essentially planar dorsal surface 25 of the stem 17 is spaced the prescribed distance Z from the lateral tip of the head 19. The stem cross section is that of a trapezoid with rounded corners, with the parallel bases lying on the dorsal and volar surfaces. The volar base is the shorter of the two. Positions along the stem 17 at about its distalmost portion are labeled as S3 and S6 respectively in FIGS. 3 and 4. Dimension S6 is greater than dimension S3, resulting in an asymmetric cross section shape stem that resists rotation. The cross sectional dimensions of the stem 17 increase from the distalmost aspect to the point where the stem 17 meets the collar 15. In FIG. 4, it can be seen that the increase in dimensions between points S5 and S4 is gradual; thus, the width of the dorsal surface 25 increases laterally, symmetrically along the length of the stem from its distalmost tip to the point where the stem 17 meets the collar 15. The width of the volar surface 33 similarly increases. In the FIG.

3 lateral view, it can be seen that the thickness of the stem in the dorsal-volar direction increases more substantially from the distalmost tip to the point where the stem 17 meets the collar 15 and particularly in the region between points S2 and S1 where the increase is more pronounced. The increasing divergence of the volar surface 33 of the stem 17 from the dorsal surface 25 and the fact that the proximal end of the stem is offset somewhat from the centerline of the collar 15/head section 13 (line a), as seen in FIG. 3, results in a stem having a distal end portion that constitutes more than one-half its length which lies totally dorsally of the centerline "a" of the implant (as defined by the head 19 and collar 15). Satisfactory exemplary interrelationships between these dimensions are set forth in the following Table which need not be exclusive:

TABLE

| Dimension Ranges |
|---|
| H = 8.0 mm-15.0 mm (0.315 in.-0.590 in.) |
| T = 1.0 mm-2.0 mm (0.04 in.-0.08 in.) |
| Y = (0.60-1.0)H |
| DW = (0.95-1.30)LW |
| DW = (1.15-1.60)H |
| N = (0.80-0.95)H |
| N = (0.95-1.3)Y |
| NR = (.06-0.10)N |
| X = (0.20-0.35)DW |
| Z = (0.09-0.20)H |
| S1 = (0.35-0.60)DW |
| S2 = (0.20-0.30)DW |
| S3 = (0.15-0.25)DW |
| S4 = (0.50-0.65)DW |
| S5 = (0.40-0.55)DW |
| S6 = (0.25-0.40)DW |

It has been found that the shaping and the proportioning of the prosthesis 11 provides a thumb metacarpal implant with a spherical head 19 that, when received in a surgically prepared cavity in the trapezium 6, will result in a repaired joint which will function in a manner substantially equivalent to the native joint. It can be seen from FIG. 8B that the implanted prosthesis 11, although unconstrained, will still excellently resist joint subluxion or dislocation and thus provide the desired joint stability. Moreover, the location of the head section 13 and collar 15 relative to the dorsal surface 25 of the stem, and the proportioning and shaping of the neck 21 which supports the head on such a preferably oblong collar of specially designed shape, results in both extension movement (see FIG. 8A) and flexion movement (see FIG. 8C) equivalent to that of the native joint.

Important in attaining these results are the dimensioning of the collar 15 and the sizing and shaping of the neck 21 which supports the spherical head. The collar 15 is generally oblong, preferably having a dorsal width (DW) which is 10% to 30% greater than its lateral width (LW), and more preferably at least 15% greater. In addition, the dorsal width (DW) should be from 15% to 60% greater than the diameter of the head and preferably at least 35% greater. In addition, the curvature of the dorsal edge 27 should be shallower than that of the volar edge 31 by at least about 20%. In combination with these proportions, the shaping and sizing of the neck 21 is of equal importance. It has been found that there is an important interrelationship between the narrowest diameter of the neck (diameter N) and both the diameter of the head 19 and the axial length of the head section 13, i.e. dimension Y. In this respect, the neck diameter N should be 80% to 95% of the spherical diameter of the head, and it should be between 95% and 130% of the axial length Y. The neck surface is preferably that of a section of a torus, which is blended for smooth transition with the flat proximal surface of the collar 15 and the spherical head 19, the radius of which torus is between 6% and 10% of the neck diameter N.

Finally, together with this shaping and proportioning of the head section 13 and collar 15, the relative location of the head and stem 17 is such that the stem, which has a dorsal, essentially planar surface 25 oriented essentially perpendicular to the flat collar, is located so that it is spaced from a parallel plane tangent to the dorsal tip of the head 19 by the distance Z. By carefully holding Z between 9% and 20% of the diameter of the spherical head 19, implantation of the prosthesis 11 in the resected metacarpus effectively positions the metacarpus 2 in precise, desired, ultimate relationship to the trapezium 6 that will replicate native joint movement. The cooperative interplay of all of the above features results in a prosthesis 11 that is surprisingly effective to repair a thumb CMC joint while retaining the major portion of the trapezium 6.

In using the prosthesis 11 to surgically repair the joint, the surrounding soft tissue is removed or displaced in order to allow a portion of the base of the metacarpus 2 to be surgically resected. The osteotomy is performed to create a resection normal to the long axis of the metacarpal bone and results in a gap between the resected base of the metacarpal bone and the articular surface of the trapezium 6. A spherical socket or cavity is then surgically formed in the trapezium 6 to a desired depth equal to about one-third to one-half of the spherical diameter of the spherical head 19 of the prosthesis that is chosen to be employed; the surgeon is able to choose from a set of such prostheses varying in head and/or stem sizes. For example, head sizes may vary from a spherical diameter of about 0.4 inch to about 0.52 inch, whereas stem length may vary from about 0.62 inch to about 0.86 inch, with three or four different combinations of sizes for each being available from which to choose. It is important that the spherical socket for the head be proportioned so as to leave an annular rim of a trapezial bone of about 2-3 mm in the original articular surface of the trapezium 6. After sizing, and perhaps implanting a test prosthesis to see if an optimum fit is obtained, the surgeon will then implant the chosen prosthesis 11 in the medullary canal of the resected metacarpus 2. The shape of the stem 17, with its flaring volar surface 33 and its planar dorsal surface 25, results in precise placement of the spherical head relative to the proximal end of the metacarpus once the distal surface of the flat collar 15 is in abutting contact with the resected base of the metacarpus. The spherical head 19 of the implant, when received in the surgically prepared cavity in the trapezium 6, provides an essentially ball-and-socket connection which is secure once the surrounding soft tissue ligaments/tendons are repositioned and/or reconnected. The ultimate repaired joint not only exhibits excellent stability in resisting subluxion and dislocation, but circumduction and axial rotation motions of the CMC joint following reconstruction with this prosthesis 11 are equivalent to that of the native joint. In other words, the shaping of the flat collar 15 and the geometry and proportioning of the neck 21, in combination with precise placement at the end of the resected metacarpus 2, achieves an interengagement between the metacarpus and the trapezium which provides a repaired CMC joint having a normal range of flexion/extension, abduction/adduction, and axial rotation motion.

While the invention has been described with regard to certain preferred embodiments which constitute the best mode presently known to the inventors, it should be understood that various changes and modifications as would be obvious to one having skill in the art may be made without departing from the invention so long as the aforesaid guidelines are maintained in the shaping and proportioning of the components. For example, although the neck 21 preferably has the afore-described double-curved surface, another implant embodiment might have a neck arcuate surface of the neck might have a surface with a cylindrical section along its length. Particular features of the invention are emphasized in the claims that are appended hereto.

The invention claimed is:

1. A hemi-arthroplasty implant for the base of the first metacarpal of the thumb CMC joint, said implant including a head section, a flat collar and a stem section, said head section comprising a spherical head and a neck section which connects said head to said flat collar, said neck section comprising an arcuate surface of circular cross section which extends between said spherical head and said flat collar, said neck section having a diameter (N) at its narrowest point of at least about 5% less than a diameter (H) of said spherical head, and said flat collar being of noncircular, shape having a dorsal edge, a volar edge and two lateral edges, with its dorsal width (DW) and its lateral width (LW) proportioned so that the dorsal width (DW) is within the range of 95% of the lateral width (LW) to 130% of the lateral width (LW), with the dorsal width (DW) being 15% to 60% greater than the diameter of said spherical head, and with both said dorsal edge and said volar edge of said flat collar being curved and said dorsal edge having a radius of curvature which is greater than the radius of curvature of the volar edge by at least about 20%.

2. The implant of claim 1 wherein said stem section has a cross section which is that of a trapezoid with rounded corners, said cross section being reduced in size in a direction proximal to distal along its length, and wherein two parallel bases of the trapezoid lie on the dorsal and volar surfaces of said stem section, with the shorter of the two bases of the trapezoidal cross section lying on the volar surface.

3. The implant of claim 2 wherein said stem section has a dorsal surface which is rectilinear and essentially planar and is spaced apart from a parallel plane that is tangent to a dorsal tip of said spherical head a distance (Z) equal to between 9% and 20% of said spherical head diameter.

4. A hemi-arthroplasty implant for the base of the first metacarpal of the thumb CMC joint, said implant including a head section, a flat collar and a stem section, said head section comprising a spherical head and a neck section of re-entrant curvature that connects said head to said flat collar, said neck section comprising an arcuate double-curved surface of circular cross section with its narrowest diameter (N) being at least about 10% less than a diameter (H) of said spherical head, and said flat collar being of oblong shape having a dorsal edge, a volar edge and two lateral edges, with its dorsal width (DW) being at least about 15% greater than its lateral width (LW), with said dorsal edge and said volar edge of said flat collar being curved and with said dorsal edge having a radius of curvature which is greater than the radius of curvature of said volar edge by at least about 20%, wherein an axial length (Y) of said head section from the proximal surface of said flat collar to a tip of said spherical head is equal to between about 60% and 100% of a diameter (H) of said spherical head and wherein the neck section narrowest diameter (N) is equal to about 0.95 the axial length (Y).

5. The implant of claim 4 wherein the spherical head is centered on said collar in both the dorsal/volar and lateral directions and wherein said neck section has a generally toroidal surface.

6. The implant of claim 4 wherein said neck has a toroidal surface which has a radius equal to between about 6% and 10% of said diameter (N).

7. A hemi-arthroplasty implant for the base of the first metacarpal of the thumb CMC joint, said implant including a head section, a flat collar and a stem section, said head section comprising a spherical head and a neck section of re-entrant curvature that connects said head to said flat collar, said neck section comprising an arcuate double-curved surface of circular cross section with its narrowest diameter (N) being at least about 10% less than a head diameter (H) of said spherical head, said flat collar being of oblong shape having a dorsal edge, a volar edge and two lateral edges, with its dorsal width (DW) being greater than its lateral width (LW), wherein an axial length (Y) of said head section from the proximal surface of said flat collar to a tip of said spherical head is equal to between about 60% and 100% of a diameter (H) of said spherical head and wherein the neck section narrowest diameter (N) is equal to about 0.95 the axial length (Y), and said stem section has a rectilinear dorsal surface that is essentially planar and that is spaced apart from a parallel plane that is tangent to a dorsal tip of said spherical head a distance (Z) equal to between 9% and 20% of said head diameter (H).

8. The implant of claim 7 wherein the spherical head is centered on said collar in both the dorsal/volar and lateral directions and wherein said neck section has a generally toroidal surface.

9. A hemi-arthroplasty prosthesis for the base of the first metacarpal of the thumb CMC joint, said prosthesis including a head section, a flat collar and a stem section, which head section comprises a spherical head and a neck section which connects said head to said flat collar, said spherical head being centered on said collar in both the dorsal/volar and lateral directions, said neck section having an arcuate surface of circular cross section the narrowest diameter (N) of which is at least about 5% less than a diameter (H) of said spherical head, and said flat collar being of noncircular shape having a dorsal edge, a volar edge and two lateral edges, with its dorsal width (DW) and its lateral width (LW) proportioned so that the dorsal width (DW) is within range of 95% of the lateral width (LW) to 130% of the lateral width (LW), and said stem section having a rectilinear dorsal surface which is essentially planar and which is spaced apart from a parallel plane that is tangent to a dorsal tip of said spherical head a distance (Z) equal to between 9% and 20% of said spherical head diameter (H).

10. The prosthesis of claim 9 wherein said neck section has a neck section diameter (N) of between about 80% and 95% of the spherical head diameter.

11. The prosthesis of claim 10 wherein the head section has an axial length (Y) from the proximal surface of said flat collar to a tip of said spherical head which is equal to between about 60% and 100% of said spherical head diameter (H) and wherein the neck section diameter (N) is equal to between 0.95 the axial length (Y) and 1.3 the axial length (Y).

12. The prosthesis of claim 9 wherein said neck has a toroidal surface with a radius equal to between about 6% and 10% of said diameter (N).

13. The prosthesis of claim 9 wherein said dorsal edge and said volar edge of said flat collar are curved and said dorsal edge has a radius of curvature which is greater than the radius of curvature of the volar edge thereof by at least about 20%.

14. A method of repairing a CMC joint, which method comprises the steps of:

(a) resecting the base of a metacarpal bone, (b) surgically cutting a socket of spherical curvature in a trapezium at the CMC joint to leave a rim of at least 2 mm about said socket, (c) implanting the stem section of a prosthesis according to claim 9 in the a medullary canal of the metacarpal bone that was resected, and (d) placing the spherical head of said prosthesis in said socket.

* * * * *